United States Patent
Brogan et al.

(10) Patent No.: US 9,993,337 B1
(45) Date of Patent: Jun. 12, 2018

(54) ORTHOPAEDIC IMPLANT AND METHOD OF MAKING SAME

(75) Inventors: Cynthia M. Brogan, Cleveland Heights, OH (US); Carl McMillin, Brecksville, OH (US)

(73) Assignee: OSTEOSYMBIONICS, LLC, Cleveland, OH (US)

( * ) Notice: Subject to any disclaimer, the term of this patent is extended or adjusted under 35 U.S.C. 154(b) by 0 days. days.

(21) Appl. No.: 12/177,138

(22) Filed: Jul. 21, 2008

Related U.S. Application Data (60) Provisional application No. 60/950,744, filed on Jul. 19, 2007.

(51) Int. Cl.
```
A61F 2/44      (2006.01)
A61F 2/02      (2006.01)
A61F 2/24      (2006.01)
A61F 2/28      (2006.01)
A61F 2/30      (2006.01)
```

(52) U.S. Cl.
CPC .............. *A61F 2/24* (2013.01); *A61F 2/2875* (2013.01); *A61F 2002/2889* (2013.01); *A61F 2002/3009* (2013.01); *A61F 2002/30011* (2013.01); *A61F 2002/30013* (2013.01); *A61F 2002/30028* (2013.01); *A61F 2002/30029* (2013.01); *A61F 2002/30065* (2013.01); *A61F 2002/30316* (2013.01); *A61F 2002/30321* (2013.01); *A61F 2002/30322* (2013.01); *A61F 2310/0094* (2013.01); *A61F 2310/00329* (2013.01); *A61F 2310/00335* (2013.01); *A61F 2310/00353* (2013.01); *A61F 2310/00389* (2013.01); *A61F 2310/00928* (2013.01); *A61F 2310/00934* (2013.01); *A61F 2310/00952* (2013.01); *A61L 2400/02* (2013.01); *A61L 2400/18* (2013.01); *A61L 2430/02* (2013.01)

(58) Field of Classification Search
CPC ............................................. A61F 2310/00353
USPC ............ 623/23.5, 17.17–17.18, 23.58–23.59
See application file for complete search history.

(56) References Cited

U.S. PATENT DOCUMENTS

| | | | | |
|---|---|---|---|---|
| 4,470,159 | A | * | 9/1984 | Peyman .................... A61F 2/16 623/5.11 |
| 5,876,447 | A | * | 3/1999 | Arnett .................... A61F 2/0059 623/17.18 |
| 5,925,077 | A | * | 7/1999 | Williamson et al. ...... 623/22.34 |
| 6,277,150 | B1 | * | 8/2001 | Crawley et al. ........... 623/17.18 |
| 7,018,418 | B2 | * | 3/2006 | Amrich et al. .............. 623/23.5 |
| 7,122,057 | B2 | * | 10/2006 | Beam et al. ................ 623/23.51 |

(Continued)

OTHER PUBLICATIONS

Jordan, Richard, D. et al., Technique for cranioplasty prosthesis fabrication, The Journal of Prosthetic Dentistry, Aug. 1978, pp. 230-233, vol. 40, No. 2, The C.V. Mosby Co., USA.

*Primary Examiner* — Jacqueline Woznicki (57) ABSTRACT

An improved polymer orthopedic implant and a method for making the same, where a portion of the implant for engagement with a patient's bone has a rough texture for encouraging micro-ingrowth between the bone and the implant. Substantially all remaining non-bone engaging portions of the implant are smooth for discouraging tissue ingrowth with the implant. The non-bone engaging portions of the implant are polished smooth, and are preferably transparent or translucent. The implant may be comprised of a slow reacting polymethylmethacrylate acrylic.

3 Claims, 5 Drawing Sheets

(56) References Cited

U.S. PATENT DOCUMENTS

2005/0288790 A1* 12/2005 Swords .................. 623/17.19
2008/0195218 A1* 8/2008 Jones ..................... 623/20.36

* cited by examiner

ORTHOPAEDIC IMPLANT AND METHOD OF MAKING SAME

CROSS-REFERENCE TO RELATED APPLICATIONS

The present application claims priority from U.S. Patent Application Ser. No. 60/950,744 filed Jul. 19, 2007, the entire subject matter of which is incorporated herein by reference.

FIELD OF INVENTION

This invention relates generally to orthopaedic implants, and more particularly to an orthopaedic implant with smooth and rough portions to optimize stability and biocompatibility, and an improved method for making the same.

BACKGROUND OF THE INVENTION

A variety of orthopaedic implants have previously been developed and are currently available for surgical implantation. A variety of metal materials, for example stainless steel or titanium, have been used for such implants. Often, where the implant is desired for bone replacement in a cranial or facial application, the implant is not generally of a standard size or configuration, and must be customized to fit the patient. In applications where such customization is advantageous, the use of metal materials, while desirable for their strength and biocompatibility, are less feasible due to the difficulty and expense of manufacture. Metal implants also obscure post-operative x-ray and MRI examination of patients, which is especially important when there has been tumor removal and it is desirable to assure no recurrence of the cancer. As a result, polymer materials have provided a desirable alternative for the manufacture of such custom implants.

One example of a custom polymer cranial implant is available from Stryker Corporation of Kalamazoo, Mich. The Stryker Custom Cranial Implant is derived from the patient's CT data, and converts the data into 3-D computer-generated images to build an anatomical model. The implant is a polymer material manufactured of 75% methylmethacrylate-styrene copolymer for strength, 15% polymethylmethacrylate (PMMA) for handling, and 10% barium sulfate for radio-opaqueness. An additional example of a craniofacial implant is offered by Porex Surgical Products Group of Newnan, Ga. The Medpor® implant is a biocompatible porous polyethylene material which allows tissue ingrowth. See www.porexsurgical.com. A still further example of a polymer implant for craniofacial applications is available from Osteopore International of Singapore. The Osteopore PCL scaffold bone filler is made from filaments of 3-D inter-woven bioresorbable polymer. This material has inter-connected pores and is said to be cell tissue compatible.

While such prior art examples of polymer implants, particularly those used in craniofacial orthopaedic applications, have had desirable results, various disadvantages remain. In craniofacial implants, it may be advantageous to avoid adhesion and tissue ingrowth of the adjacent external and internal tissue, while at the same time encouraging bone ingrowth with the implant along the edges of the implant engaged with the skull. An implant of the prior art having all porous surfaces provides for boney ingrowth at the edge for stability but also has the disadvantage of allowing superior and inferior surfaces tissue ingrowth and/or adhesions. Prior art implants having smooth surfaces also failed to optimize boney fixation at the edge of the implant.

SUMMARY OF THE INVENTION

The present application provides a new and improved orthopaedic implant, specifically an orthopaedic implant with at least two different surface textures, both a smooth portion on a superior and inferior surfaces and a rough portion on the edges, to optimize the stability and biocompatibility of the implant, and a method for making the same. The implant of this application is preferably provided of high or medical grade polymethylmethacrylate (PMMA) or acrylic, for use in craniofacial applications, but could also be provided of other biocompatible polymers, such as the polyarylether ketones, including for example polyetheretherketone (PEEK), polyetherektoneketone (PEKK) and polyetherketoneetherketoneketone (PEKEKK), or of metals including, for example, titanium and stainless steel, and is provided with smooth surfaces, and ceramics including for example hydroxylapatite or bioglass.

The implant superior and inferior surfaces, meaning substantially all non-bone engaging implant surfaces, are smooth in order to allow tissue, such as the scalp, to move adjacent to the implant and to discourage or reduce dural and tissue adhesions. The rough textured surface is provided at the perimeter of the implant to enhance stability and to allow for bony in-growth or attachment of the implant to the skull along their engagement surfaces. The rough texture is preferably a beveled, etched or sanded edge, created to allow best fit engagement of the implant with the bone and micro-ingrowth of skull tissue with the implant. The smooth surfaces of the implant, or the scalp and dura surfaces, are solid, smooth and non-porous to discourage tissue ingrowth, adhesion ingrowth and non-vascularized infection sites. Additionally, the use of PMMA can result in an implant of a clear or transparent material, which enables the surgical site beneath the implant to be as visible as possible during the implantation procedure and during any necessary post-operative inspections. If surgeons so desire, the implant can made translucent, opaque, and/or radio-opaque by this method. The use of such a PMMA material is desirable for: i) use of the least material additives, enabling increased biocompatibility; ii) ease of cutting of the material (instead of melting) during post-cure adjustments by either manufacturers or the implant surgeon, and during processing of the edge; iii) longer working time during the initial processing by the manufacturer which provides greater flexibility and tolerance for technician skill; iv) clear color which allows optimal viewing of the surgical field; and v) a clear color without blue or yellow tones which enables an untainted view of the surgical field.

A method for manufacturing the polymer implants of the present application is also provided. The present method makes use of high grade or medical grade polymethylmethacrylate with few additives and a slower cure rate which permits additional implant design modifications to be made.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION OF THE PREFERRED EMBODIMENTS

Figure 9:
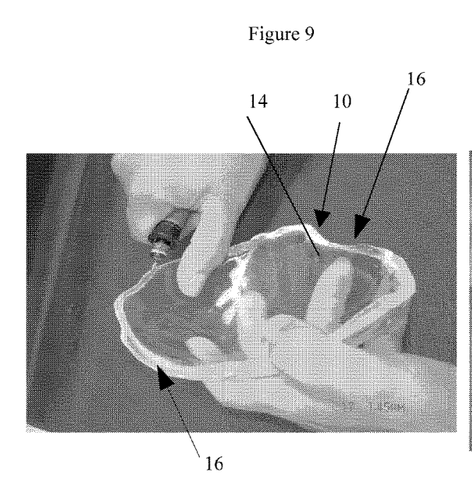
FIG. 9 illustrates a transparent embodiment of the implant of the present application having a textured surface created at the edge of the implant for improved engagement with the patient's bone.
Figure 12:
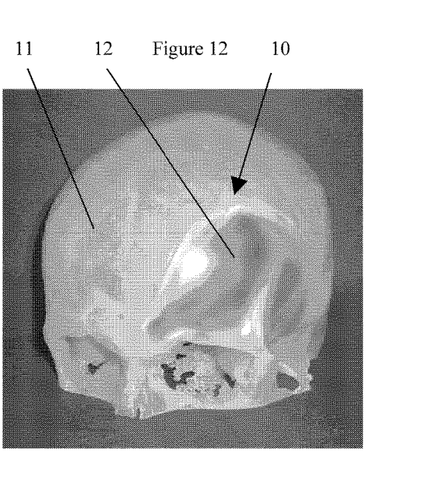
FIG. 12 illustrates a translucent embodiment of the implant of the present application engaged with the model shown in FIG. 9.

The present application provides an improved orthopaedic implant and method of making the same. As shown in FIGS. 9 and 12, a clear, transparent or translucent implant 10, respectively, is provided which is manufactured of polymer material having smooth surfaces, for example, a smooth superior surface 12 and a smooth inferior surface 14, and an etched or rough textured surface 16 where the implant engages the patient's bone. Where the implant is a facial or jaw implant, numerous smooth surfaces may be provided, depending on the shape of the implant.

Custom, patient-specific implants, including craniofacial implants according the present application, are made from a polymer material. Examples of two acceptable families of polymer implant materials include polymethylmethacrylates or acrylics (PMMA) and polyarylether ketones such as polyetheretherketone (PEEK), polyetherketoneketone (PEKK) and polyetherketoneetherketoneketone (PEKEKK). Other biocompatible materials, including other plastics, metals, and ceramics would also be acceptable.

Where the polymer materials are supplied as a powdered material, they may be molded as described herein to create the implant prototype. Alternatively, the polymer materials may be injection or compression molded to shape, or supplied in a solid block of purchased raw material and then further manufactured into the desired shape with appropriate surface adjustments by processes such as milling, grinding, and polishing. An example of acceptable high grade or medical grade polyetheretherketone (PEEK), is available, for example, as KETRON® PEEK-CLASSIX LSG, from Boedeker Plastics, Inc., Shiner, Tex., www.boedeker.com. Acrylics, for example, as medical grade materials, are available as cranial bone cements, such as Johnson & Johnson Cranioplastic™, medical acrylics such as those available from Robert Scott Ocularists of Florida, Inc., from Spartech Polycast, Stamford, Conn., www.spartech.com, commercial acrylics available from Degussa Corporation, and more preferably as orthopaedic and dental acrylics from Esschem, Linwood, Pa., www.esschem.com.

Figure 1:
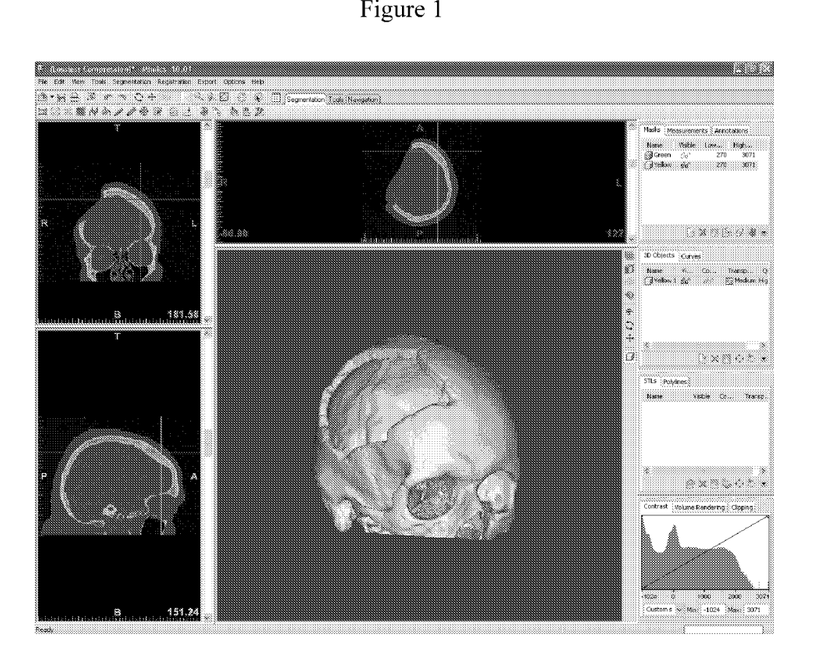
FIG. 1 illustrates a computer screen image of the computer software used to convert the two dimensional CT scan data files of the patient requiring an implant into a computer data file used for creating a three dimensional model of a portion of the patient requiring the implant.
Figure 2:
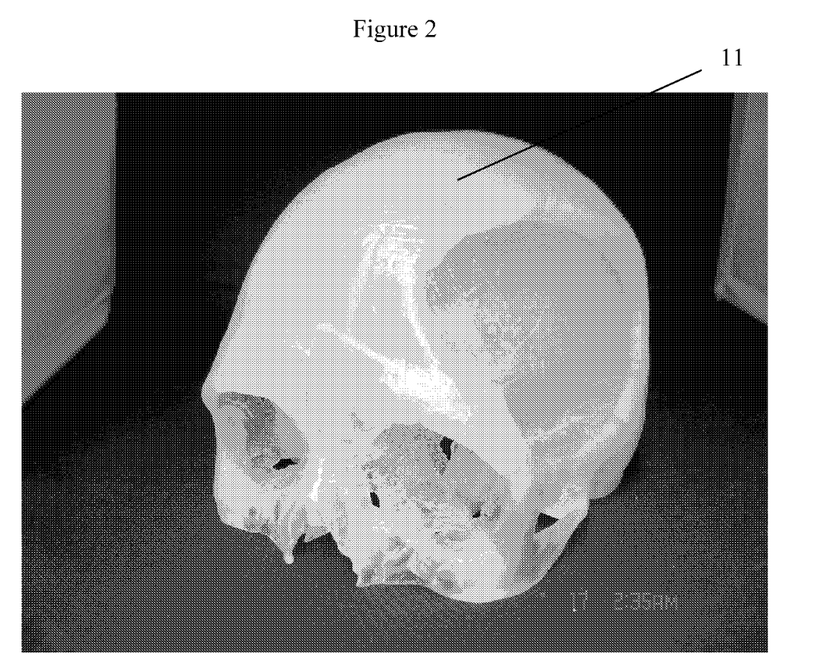
FIG. 2 illustrates a model of the portion of the patient requiring the implant, which is created using rapid prototyping techniques.

Preferred manufacture of the implant of the present application involves the following procedures. Patient-specific CT scans are received in any available electronic format from a physician desiring a customized implant. Using the patient specific CT scans, a three-dimensional anatomical model or electronic image of the patient's bone structure requiring the prosthesis is created on the computer, as shown in FIG. 1. That patient specific electronic image is saved in the computer in an industry interface standard format, an STL file. Using rapid prototyping technology, such as stereolithography (SLA) or other desirable high detail technologies, a plastic model of the patient's skull 11 or other anatomy is then built, as shown in FIG. 2.

The quality of the CT scan provided directly impacts the quality of the prosthesis. To obtain the best scan data, patient movement should be avoided. Image distortion from motion artifact will severely compromise the accuracy of the model and prosthesis. If patient motion occurs the scan should be restarted. The scans should be acquired at a high spatial resolution. The entire study or electronic scan should be saved, preferably in uncompressed DICOM format, to a removable medium such as CDs or Optical Disks. It is also possible to transfer image data via a secure computer network.

More specifically, no contrast is needed when acquiring the scan data. The data must be acquired in a single pass, without pause. In older CT scanners, slice-by-slice acquisition should be used. CT scanners may be able to acquire the data in a single spiral acquisition. For spiral scans, use a fine pitch. Do not use multiple spiral acquisitions. The slice spacing or thickness should not have gaps or overlaps. Slice thickness should be the same as slice spacing, preferably 1.0 mm or smaller, but 1.5 mm is acceptable and 2.0 mm is useable. The slice range should cover the range from air above the patient anatomy being scanned to 2 cm below the defect edge, encompassing the entire defect. The field of view should be as small as possible, but large enough to encompass the entire structure being scanned. There should be no gantry tilt, and the power setting should be approximately 125 kV, with the amperage mAs set to be sufficient for soft-tissue discrimination.

Using Mimics medical imaging computer software, available from Materialise Group of Leuven, Belguim, Ann Arbor, Mich. or www.materalise.com, or other commercially available software, the two dimensional CT scan data files generate a three dimensional image, model 11 and computer data file of the location where the patient requires the implant. The Mimics software is preferably used on a commercially available Windows based computer system having a CPU, computer screen and printer. A network connection may also be provided to transfer image data. A sample of a screen image from the Mimics software showing the three dimensional image of a patient's skull requiring an implant is shown in FIG. 1.

To reconstruct the scan data within the Mimics medical imaging computer software, a standard filter should be used and not a bone filter. For spiral acquisitions, one of the CT scanner's default slice spacing should be used. For example, if a spiral acquisition has a step size of 0.625 mm, reconstruct at 0.625 mm or 1.25 mm increments.

Figure 11:
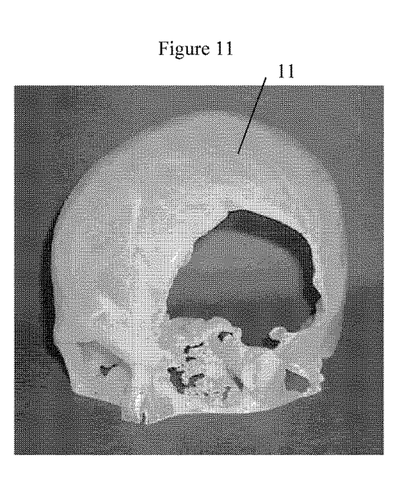
FIG. 11 illustrates a further example of a model of a patient's skull requiring an implant.

The resulting electronic data file is saved, and provided by Mimics software in STL format ready for use by a conventional rapid prototyping machine, such as a SLA or stereolithography machine or 3D printing. Using the patient specific data file, a plastic anatomical model of a patient-specific skull 18, shown in FIGS. 2 and 11, requiring the implant is generated of RenShape® SL 7810 material, available from Huntsman Corp. of The Woodlands, Tex.

Figure 3:
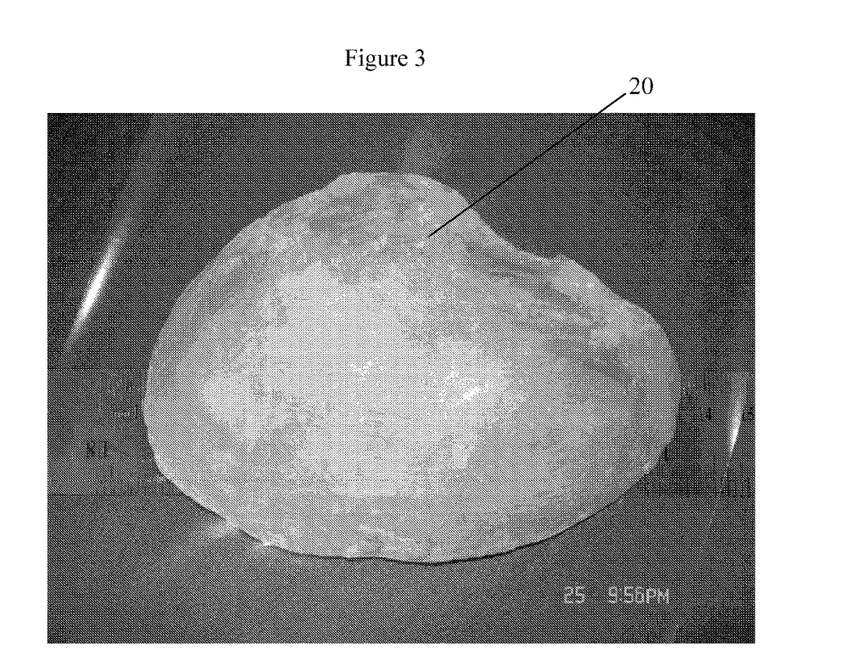
FIG. 3 illustrates a wax model of the implant of the present application created to fit the model of the portion of the patient requiring the implant.

Once the defect or location for the implant is generated in the data file using the anatomical model of the patient, an implant is designed using Mimics computer software or other commercially available software. Using one of several methods, the design of the implant may be computer generated and the prototype built using rapid prototyping technology. Alternatively, a trained medical artist may hand sculpt the implant prototype. Their skills allow them to effectively design implants for patients with asymmetric skulls or defects where there isn't an opposite side to mirror, such as bilateral craniotomies and frontal defects. The skilled technician may manually craft the implant model or prototype 20 in a wax material of the type available from Zahn Dental Laboratories, www.zahndental.com, as shown in FIG. 3. Where the prototype 20 is to be machine generated, the electronic data file containing the implant specification is sent to a rapid prototyping machine to generate an implant prototype made of the same materials as the skull model, Huntsman RenShape SL 7810. For molding of the implant, the polymer materials may be supplied as a powdered material, which is made into a slurry and molded as described herein to create the implant prototype. Alternatively, the polymer materials may be supplied in a solid block of purchased raw material, and ground to the desired shape using rapid prototyping technology or machines and the computer data file created for the implant from the CT scan files. Using this technique, there is no need for an implant prototype, and the polymer material is formed directly to the desired implant shape.

Figure 4:
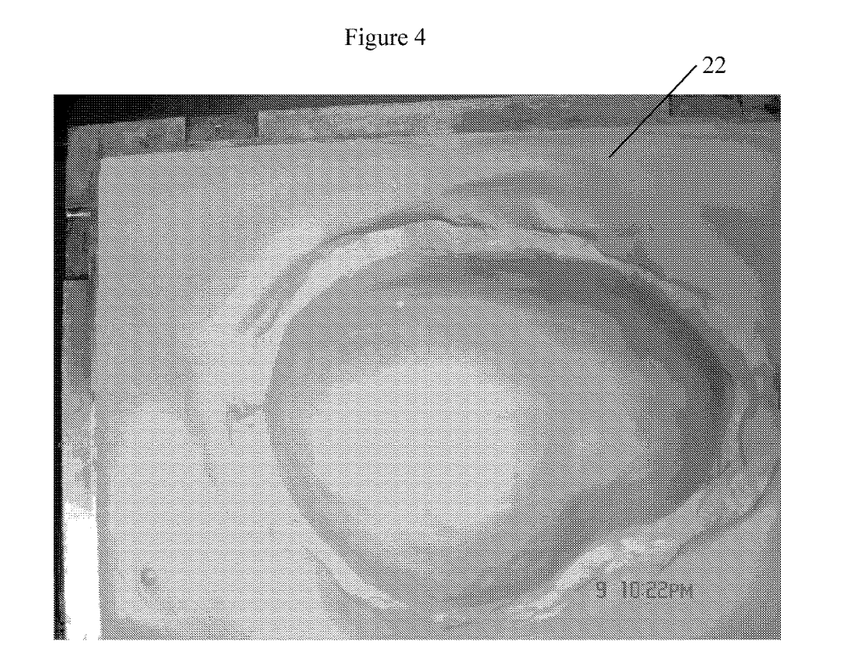
FIG. 4 illustrates the negative mold created using the wax model of the implant.

To mold the implant 10, the wax model or prototype 20 in FIG. 3, is used to create a two piece negative mold M. The mold plate 22, as shown in FIG. 4, is created by mixing and pouring dental stone into one-half of a two piece mold and placing the prototype into the slurry. Care is taken to shape the stone around the edges of the implant while the dental stone is still in a soft state. Once the dental stone has hardened, a mold release agent, such as petroleum jelly, is placed on the surface. The other half of the mold or flask is filled with dental stone and the two halves of the flask are placed together with excess dental stone extruding from the perimeter. Once the dental stone cures, which normally takes approximately 30 minutes, the mold is opened and the implant prototype removed.

Figure 5:
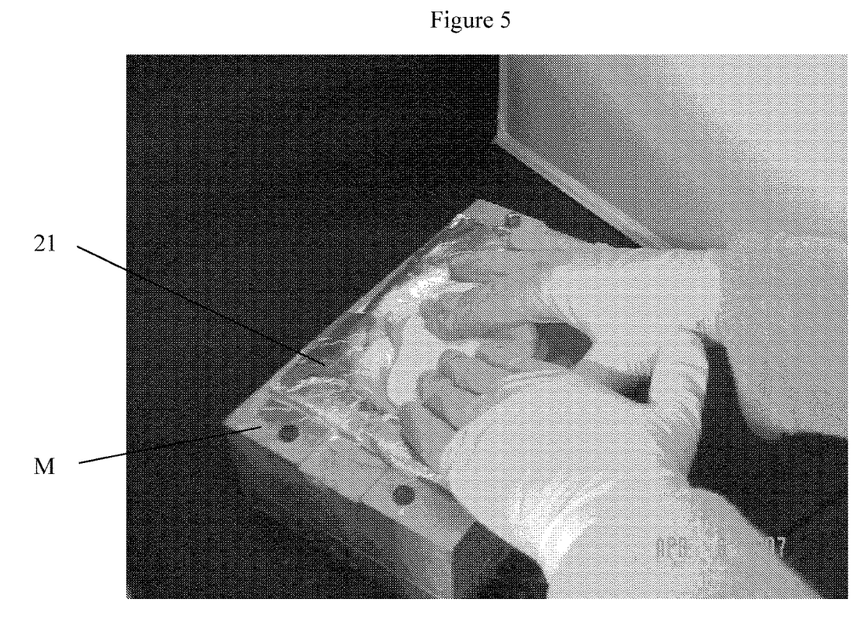
FIG. 5 illustrates one half of the mating positive mold created from the negative mold, and showing the positive mold being filled with PMMA.
Figure 6:
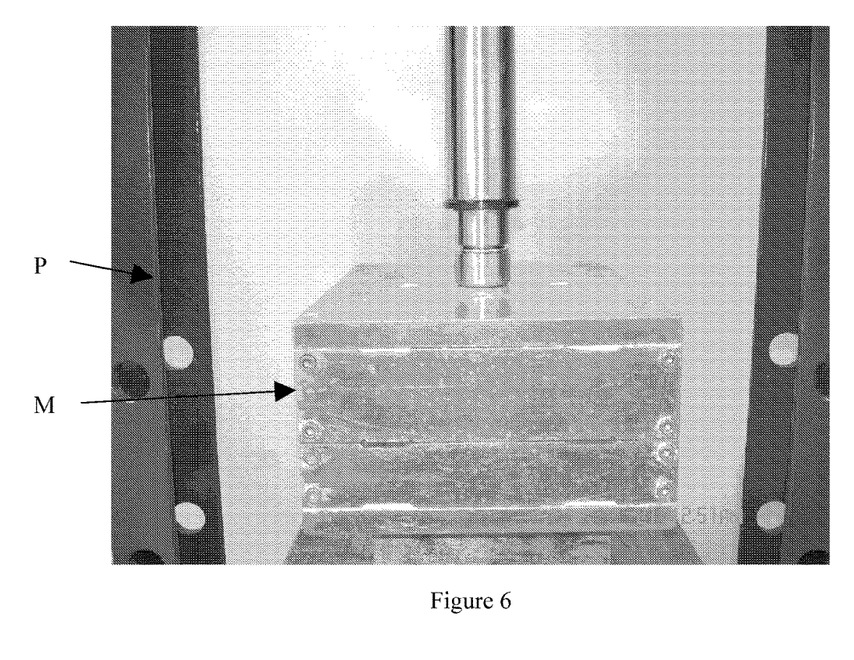
FIG. 6 illustrates the mold containing the PMMA being compressed under appropriate pressure in a mold press.

A mold release 21, such as Al-Cote Separating Agent or tinfoil, is then applied to coat or over the surface of the mold plates. The uncured PMMA, which has been mixed to form a slurry, according to manufacturer specifications from the powder supplied, and is placed into the shape of the implant in the mold plates 22, as shown in FIG. 5. The amount needed is estimated based on the size of the implant and can range from 20 mg to 400 mg. The necessary waiting times are then observed before the two piece mold is secured together and placed in the mold press P shown in FIG. 6. Within the press, the mold and PMMA are subjected to the necessary pressure to extrude excess material from the mold. It is noted that a slower cure time is desired for enabling flexibility in fabrication and allowing for different technician skills. Such slower cure times are generally obtained using a PMMA material having less additives.

Once the excess PMMA has been extruded, the flask containing the mold and PMMA goes through a heat cure process following the manufacturers instructions. Once the cure time at the necessary heat is passed, the mold is removed from the press and allowed to cool.

Figure 7:
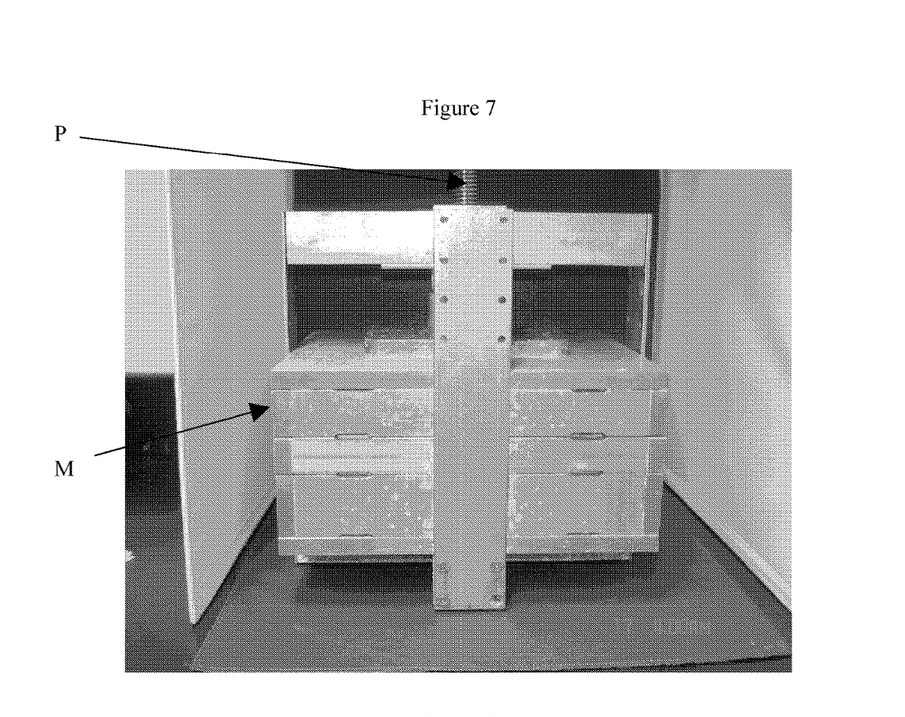
FIG. 7 illustrates the mold containing the PMMA being compressed under appropriate pressure in a flask within a mold press.

In an alternate curing process, the illustrated curing flask apparatus 30 in FIG. 7 may be used. Pressure and heat are used within a conventional press or curing equipment to cure the PMMA material within the mold for the appropriate cure time. The flask apparatus 30 shown in FIG. 7 includes a frame with panels forming a box like structure for securing the mold therein, and for placement within a curing press. Specifically, the flask apparatus is used inside the curing press, where cure times may be up to 8 hours under pressures as great as great as 440 psi, which may create expansion forces of up to 30,000 lbs for a large flask (8×10 sqin), depending on the surface area of the implant. The flask is the large metal plate rectangle positioned in the center of the thinner, upright slats. The improvement is that the flask can be disassembled allowing one to keep the mold inside. With conventional flasks you knock out or hammer out the mold which destroys the mold. The improved flask can simply be dismantled, keeping the mold inside for reuse at a later date. An extra spacer that allows one to increase the depth of the flask is also provided. Lastly, the flask is very large compared to conventional flasks, or approximately 8 inches×10 inches×5 inches. In another alternative, a PMMA formulation typically used as a bone cement for cranial repairs in the operating room can be used. Once bone cement is placed in the flask and put under pressure to extrude excess PMMA, it is held in that position and goes through a self-actuated curing process.

Figure 8:
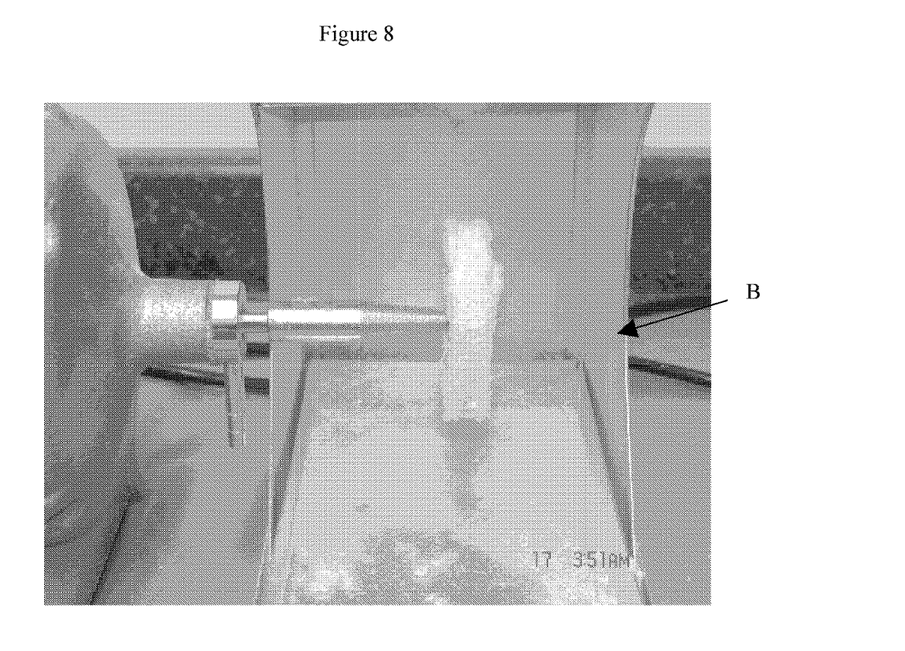
FIG. 8 illustrates the polishing and buffing wheel used to create the final smooth surface finish of the implant of the present application.

Once the implant has been cured, the mold is opened and the implant is removed. The implant is trimmed of any flash, and the surfaces are sanded using sandpaper of different grits ranging from P100 to P300, buffed using pumice such as Whip-Mix pumice, and polished, for example using Fabulustre polishing agent, to obtain a surface finish on the non-bone engaging surfaces of the implant which is a smooth, glossy-glass-like surface. A conventional polishing tool B of the type shown in FIG. 8 is used for this processing. The smooth surface created on the implant allows the tissue adjacent the implant to move, and thereby discourages tissue and adhesion ingrowth, and also resists non-vascularized infection sites.

Figure 10:
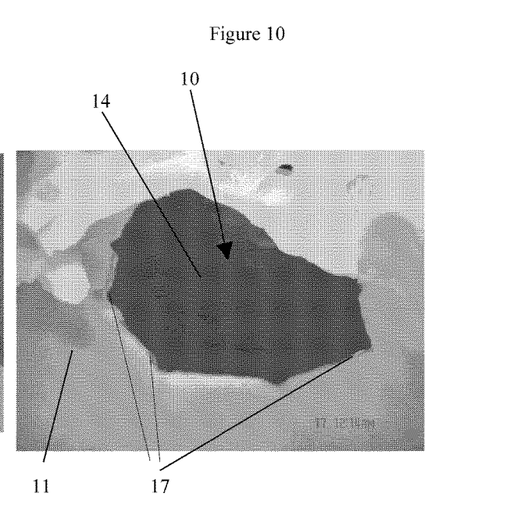
FIG. 10 illustrates an internal view of a transparent embodiment of the implant of the present application, showing a gap with the textured surface created at the edge of the implant for improved engagement with the illustrated patient's skull of the type shown in FIG. 2 or 12.

Finally, the edge 16 of the implant which engages or intersects the patient bone is beveled and etched to complement the contour of the neighboring bone as defined in the patient-specific anatomical model. Providing a rough texture to the perimeter of the implant allows micro ingrowth of bone into the implant. Substantially all of the remaining, non-bone engaging portions of the implant are smooth portions, and serve to avoid bone and other tissue ingrowth which may not be desired in other portions of the implant. The perimeter of the implant is etched, as shown in FIG. 9, using a conventional Dremel tool. The etching, or application of a rough surface texture, is preferably at least 300 microns or more, to encourage bone and tissue ingrowth. As shown in FIG. 10, the implant 10 includes the rough textured surface or edge 16 for engagement with the patient's bone. As shown in FIG. 10, the inferior surface 14 and edge surface 16 are slightly spaced from the bone (or anatomical model) to provide a slight gap 17 along the inferior surface of the implant 10. As shown in FIG. 12, the superior surface 12 is engaged with the edge surface 16, which is also beveled in a manner to enable a slight overlap over the edge of the bone, or anatomical model 11, as shown. This engagement provides a secure fit between the implant 10 and the patient's bone, particularly upon bone ingrowth to fill in the gap 17.

During implantation surgery, the implant is secured to the patient's bone using standard surgical plates and screws, as may be necessary to secure the implant.

The following examples further describe the invention but, of course, should not be construed as in any way limiting its scope.

Example 1

Successful use of the implant of the present application was provided when a tumor resection in patient resulted in a large, right parietal defect with frontal and temporal involvement. The implant provided the structural requirements for protecting the brain, and restored the natural form of the patient's cranium.

Example 2

A gunshot wound in a patient resulted in the loss of portions of the frontal, left parietal, left temporal bones, the entire left orbital roof and large parts of the left superior orbital rim and medial orbital wall. In this example, a single implant of the present application was created to replace the missing bones and orbital socket while restoring the patient's natural appearance.

Example 3

A patient with an expansile destructive lesion of the anterior left zygomatic arch with some deformation of the inferolateral wall of the left orbit. Prior to surgery, the skull model was marked to indicate portions of the skull to be replaced. In this situation, an implant was designed and produced before excision of the diseased tissue, allowing excision and replacement in one procedure.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A polymer orthopaedic implant comprising;
  a solid block of polymer medical grade implantable polymethylmethacrylate acrylic bone cement material having a rough textured portion for engagement with a patient's bone to encourage micro-ingrowth between the bone and the implant; and
  a smooth transparent surface immediately adjacent the rough textured surface on a non-bone engaging portion for discouraging tissue ingrowth with the polymer implant.

2. A polymer craniofacial implant comprising;
  a transparent solid block of medical grade implantable polymethylmethacrylate acrylic polymer material having a first smooth superior surface and a first smooth inferior surface; and
  a rough textured edge surface intermediate the first smooth superior surface and the first smooth inferior surface of the implant to engage a patient's bone is provided for encouraging micro-ingrowth between the bone and the implant.

3. An orthopaedic implant comprising:
  a single solid block of medical grade implantable polymethylmethacrylate acrylic material having a beveled and rough textured surface on a portion of the implant for engagement with a patient's bone to encourage micro-ingrowth between the bone and the implant, and
  first and second smooth surfaces adjacent the rough textured surface on a non-bone engagement portion of the implant to discourage tissue attachment and adhesions, and a portion of the implant having the first and second smooth surfaces of the implant is transparent.

* * * * *